US010039465B2

(12) United States Patent
Schultz (10) Patent No.: US 10,039,465 B2
(45) Date of Patent: Aug. 7, 2018

(54) METHOD FOR AUTOMATICALLY EVALUATING AN ABSENCE EEG, COMPUTER PROGRAM AND EVALUATING DEVICE THEREFOR

(71) Applicant: Arthur Schultz, Adelheidsdorf (DE)

(72) Inventor: Arthur Schultz, Adelheidsdorf (DE)

( * ) Notice: Subject to any disclaimer, the term of this patent is extended or adjusted under 35 U.S.C. 154(b) by 275 days.

(21) Appl. No.: 15/021,352

(22) PCT Filed: Jan. 27, 2015

(86) PCT No.: PCT/EP2015/051593
§ 371 (c)(1),
(2) Date: Mar. 11, 2016

(87) PCT Pub. No.: WO2015/121059
PCT Pub. Date: Aug. 20, 2015

(65) Prior Publication Data
US 2016/0220136 A1      Aug. 4, 2016

(30) Foreign Application Priority Data

Feb. 13, 2014  (DE) ........................ 10 2014 101 814

(51) Int. Cl.
*A61B 5/04*        (2006.01)
*A61B 5/00*        (2006.01)
*A61B 5/0476*      (2006.01)

(52) U.S. Cl.
CPC ........ *A61B 5/04012* (2013.01); *A61B 5/0476* (2013.01); *A61B 5/721* (2013.01); *A61B 5/7264* (2013.01); *A61B 5/4094* (2013.01)

(58) Field of Classification Search
None
See application file for complete search history.

(56) References Cited

U.S. PATENT DOCUMENTS 6,011,990 A  *  1/2000  Schultz ................ A61B 5/0476
600/544

FOREIGN PATENT DOCUMENTS

DE     196 08 733 C1     5/1997
WO     97/15013 A2       4/1997

OTHER PUBLICATIONS

Schultz et al., "Age-related effects in the EEG during propofol anaesthesia", ACTA Anaesthesiologica Scandanavia, Jan. 12, 2004, pp. 27-34, vol. 48, No. 1.

(Continued)

*Primary Examiner* — Etsub Berhanu
(74) *Attorney, Agent, or Firm* — W&C IP (57) ABSTRACT

The invention relates to a method for automatically evaluating an absence EEG, wherein EEG curves are recorded by an evaluating device and are evaluated by means of a computer of the evaluating device, wherein in the evaluation at least the current stage of the absent state is determined from the EEG curves by means of the computer on the basis of a stage division of the absence EEG, wherein stages of the depth of the absent state are distinguished in the stage division, and wherein the current stage is output, wherein a certain scheme of the stage division is selected by the computer from a plurality of selectable schemes of stage divisions, which differ in the number of distinguishable stages of the absent state, and is used for the automatic performance of the stage division in order to determine the current stage. The invention further relates to a computer program for performing such a method and to an evaluating device for evaluating an absence EEG.

14 Claims, 3 Drawing Sheets

(56) References Cited

OTHER PUBLICATIONS

Lamas et al., "Assessing sedation in critically ill children by bispectral index, auditory-evoked potenntials and clinical scales", Intensive Care Medicine, Jul. 4, 2008, pp. 2092-2099, vol. 34, No. 11.

Jonghe et al., "Using and understanding sedation scoring systems: a systemic review", Intensive Care Medicine, Mar. 1, 2000, pp. 275-285, vol. 26, No. 3.

* cited by examiner

METHOD FOR AUTOMATICALLY EVALUATING AN ABSENCE EEG, COMPUTER PROGRAM AND EVALUATING DEVICE THEREFOR

The invention relates to a method for automatically evaluating an absence EEG in accordance with claim 1. The invention furthermore relates to a computer program for carrying out such a method in accordance with claim and to an evaluation device for evaluating an absence EEG in accordance with claim 12.

In general, the invention relates to the field of the automated evaluation of an absence EEG, as is already described on the basis of WO 97/15013 A2, WO 2010/034305 A1 or WO 2010/034270 A1. Here, EEG is the abbreviation of the term electroencephalogram. Here, computational methods, e.g. statistical methods, are used to undertake a class division of the EEG from EEG curves, i.e. from values of EEG signals of a patient recorded successively in time, in which the current depth of the absence state of the patient is determined and a current stage of the absence state is established and output on the basis of the class division. Here, an absence state is understood to mean any state of the patient, in which the latter is not responsive/contactable in a manner appropriate for their age, or only responsive/contactable to a restricted extent; this is the case if the patient is not in the awake state.

Typical absence states are present, for example, under anesthesia, for example during an operation, or in the case of any other sedation of the patient. In this case, a patient is anesthetized or sedated by the supply of anesthetics. In general terms, anesthesia and sedation are states caused by the administration of sleep-inducing medicaments. If intensive care patients receive sleep-inducing medicaments, this is generally referred to as sedation. However, the term sedation is not restricted to intensive care patients. By way of example, if patients obtain sleep-inducing medicaments at a low dose during diagnostic interventions, this is also referred to as sedation. To this end, sleep-inducing substances to be administered e.g. intravenously are given. Alternatively, volatile anesthetics based on flurane, such as sevoflurane, can be used during anesthesia and sedation. With increasing dose, these can trigger seizure potentials, which can be identified and, where necessary, masked in the recorded EEG curves in the case of an appropriate evaluation, as already explained in the aforementioned prior art.

Further typical absence states are present, for example, in the case of a coma or in many further states during intensive care, i.e. in an intensive care unit (intensive care EEG). Intensive care patients can have very different disorders, which may influence the brain function. Typically, there is progressive deceleration in the EEG with an increase in the damping of the brain function. Depending on the degree of the deceleration, it is possible to distinguish between different stages, e.g. A to F. Decelerations to stage F can be caused by e.g. metabolic decompensation, hypothermia, oxygen deficiency.

In general, the term absence EEG or absence state therefore comprises cases in which the brain function of a patient is modified within the meaning of damping compared to a normal state. In addition to the above-described scheme of deceleration, special patterns, such as epilepsy-typical activity, may occur in the EEG.

The detected EEG curves moreover are subject to certain changes as a result of a progressive development of a person. Particularly striking changes can be observed in the development of young people, i.e. of children, up to the transition into the adult age. The EEG curves develop very markedly particularly within the first year of life.

WO 97/15013 A2 has already disclosed that the EEG of a human has age-dependent characteristics. What was proposed therein to improve the stage division was to select the age-specific classification functions for a subject from different stored age-dependent classification functions. As a result of this, it is possible to make the correct stage division in a more reliable manner.

It is intended that the known method be improved further in order to enable a reliable determination of the current stage of the absence state, in particular in the case of very young patients within their first years of life.

In accordance with claim 1, this object is achieved by a method for automatically evaluating an absence EEG, in which EEG curves are recorded by an evaluation device and evaluated by means of a computer of the evaluation device, wherein at least the current stage of the absence state of a patient is determined during the evaluation from the EEG curves by means of the computer on the basis of a stage division of the absence EEG, wherein a distinction is made in the stage division between stages of the depth of the absence state, and wherein the current stage is output, wherein a specific scheme of the stage division is selected by the computer from a plurality of selectable schemes of stage divisions, which differ in terms of the number of distinguishable stages of the absence state, and it is used for automatically carrying out the stage division for determining the current stage. The invention is advantageous in that a development- or age-adapted stage division of the absence EEG can be carried out and appropriately adapted information can be displayed to the user. These are determined with a high reliability. Hence, in particular, a flexible adaptation to very young patients can take place. As shown in very recent findings, only a few absence EEG states are distinguishable in newborns or very young children. The number of distinguishable stages increases depending on the maturity of the brain.

By way of example, the evaluation device can be embodied as a compact device which is arranged in the vicinity of a patient. The evaluation device can also be embodied as a device consisting of a plurality of components, wherein the components may also be arranged in a distributed manner, e.g. in different rooms of a building. By way of example, the evaluation device can thus have a data recording station for recording the EEG curves and, arranged at a distance therefrom, a computer, e.g. a central computer in an intensive care unit, for an online evaluation of the EEG curves or a computer for an offline evaluation of the EEG curves.

In accordance with one advantageous development of the invention, provision is made for checking, after the start of the absence state, whether the EEG curves have certain features, on the basis of which a decision can be made as to which scheme of the stage division is used thereafter. The selection of the specific scheme from a plurality of selectable schemes of stage divisions can therefore take place once, shortly after the start of the absence state. It is also possible to continue to analyze the EEG curves during the absence state in respect of features, on the basis of which the scheme of the stage division is to be selected, and, in the subsequent operation, still change from a once selected scheme to another selected scheme where necessary.

The current stage of the absence state determined on the basis of the selected scheme of the stage division is output in the process, for example by virtue of being transferred to another device by way of an interface of the evaluation device or by virtue of being visually depicted directly on the evaluation device, for example on a display. In accordance with an advantageous development of the invention, information about the currently selected scheme of the stage division is additionally output, for example by way of an output to the aforementioned interface or by way of the visual depiction on the evaluation device. This allows the user of the evaluation device to make a quick and intuitive assessment of the output data.

Various methods and algorithms are possible for the evaluation of the EEG curves by means of the computer and for the stage division of the absence EEG, of which some are explained below in an exemplary manner.

Electroencephalography is a method for displaying electric activity generated by the brain. In a conventional manner, the EEG is registered by means of a multichannel writer on endless paper. Increasingly, recording is also undertaken with the aid of computers.

The composition of the waveforms in the electroencephalogram (EEG) is dependent on the functional state of the brain. The EEG images which occur in patients in the field of surgery and intensive care are multifaceted and can be influenced by a large number of endogenous and exogenous factors. In addition to the normal awake EEG, e.g. elements of the sleep EEG, effects of medicaments and other exogenously supplied chemical substances, ventilation-dependent and metabolic influences, temperature effects, consequences of traumatic brain lesions and inflammatory, vascular, degenerative EEG changes and EEG changes caused by neoplasms are to be expected.

The following frequency ranges are associated with the waves occurring in the EEG: alpha (7.5-12.5 Hz), beta (>12.5 Hz), theta (3.5-7.5 Hz) and delta (0.5-3.5 Hz). Additionally, it is possible to delimit the sub-delta (<0.5 Hz) and the gamma band (>30 Hz). In the findings, the waves in frequency ranges are described in view of their amplitudes, frequency, regularity, temporal structure, spatial distribution and change in the case of stimuli. EEG amplitudes are measured in μV. Higher frequency waves generally have smaller amplitudes, while an increase in amplitude is usually connected with deceleration.

For the purposes of classifying sleep, anesthesia and coma EEG stages, Kugler proposes an EEG division, in which the awake state is denoted by A and EEG images with progressive damping of the brain function are denoted by the letters B to F. For the purposes of assessing the EEG curves, the frequency and amplitude of the waves in specific frequency ranges and typical patterns are used.

The awake EEG, stage A, is characterized by waves in the alpha frequency range in the majority of adults. Stage B is characterized by waves with a quick frequency and low amplitude. Theta and delta waves occur in stages C and D. In stage E, the curve image is determined by high-amplitude delta activity. Stage F is characterized by a change between flat to isoelectric curve intervals and groups of higher waves, the burst suppression pattern, or by a continuous, very flat activity.

The derivation of a conventional EEG is relatively complicated. The interpretation requires specialist knowledge and experience. A better assessment of the dynamically progressing EEG change is made possible by recording the original signal and the EEG spectral analysis. For the purposes of calculating an EEG power spectrum, the EEG signals, after analog-to-digital conversion, are subjected to e.g. a Fast Fourier Transform (FFT) for a defined time interval. With the aid of the Fourier transform, the wave pattern of the EEG is decomposed into underlying oscillation components; there is a conversion from the time to the frequency domain. The squared amplitudes of the oscillation components form the power spectrum. The frequencies occurring in the time signal can be read off in the EEG power spectrum. However, these specifications also require interpretation in order to obtain information about the EEG stage and, hence, about the cerebral functional state.

The further processing of the results of the Fourier transform comprises the extraction of so-called spectral parameters and further statistical calculations. The parameters that can be derived from the spectrum include, for example, the overall power and absolute and relative power in different frequency bands. Further parameters that are often used are the median, the spectral edge frequency and the dominant frequency. The median is the frequency at which the area of the spectrum is divided into two equal parts. The spectral edge frequency is usually defined as 95% quantile, i.e. 95% of the overall power of the spectrum lie below this frequency. The dominant frequency is the frequency with the highest power.

By way of the power spectrum, the frequency distribution of EEG sections can be displayed in a clear manner. By contrast, specific patterns, such as burst suppression phases or seizure potentials, generally cannot be deduced from the spectrum.

The Fast Fourier Transform (FFT) is a method for the quick calculation of the power spectrum.

A possibility for analyzing EEG signals in the time domain lies in the establishment of autoregressive parameters. Autoregressive (AR) parameters are variables from the time domain. A measured value at a specific time is represented as a weighted sum of the past values thereof plus a random component. The weights are the AR parameters. The general equation for an AR process is:

$$Y_t = a_1 * Y_{t-1} + \ldots + a_p * Y_{t-p} + e_t.$$

Here, $Y_t$ denotes the measured value at the time t, $a_i$, $i=1, \ldots, p$ denote the AR parameters and $e_t$ denotes independent random components with a mean value of 0 and the constant variance for all times t. The letter p denotes the order of the process, i.e. the number of past values which are taken into account. The model parameters can be estimated with the aid of the Yule-Walker equation. The approach by Box and Jenkins is usually used to establish the order of the model and to test the model quality. An overview of further estimation methods and model classes is provided by Kay and Marple.

A frequently employed method for characterizing EEG measurements lies in the calculation of specific EEG parameters, which have been proposed by Hjorth and named after him. Here, this relates to three parameters, namely activity, mobility and complexity. The Hjorth parameters are calculated from the spread of the EEG signal and the first and second derivative thereof. Alternatively, the Hjorth parameters can also be calculated in the frequency domain, i.e. with the aid of the spectral analysis.

The activity corresponds to the overall power of the signal and is therefore a measure for the size of the amplitude of the EEG measurement. The mobility can be interpreted as a measure for the mean frequency and the complexity as a measure for the variability of the signal.

In addition to pure spectral parameters or pure AR parameters, the combined establishment of e.g. spectral parameters, AR parameters, Hjorth parameters or else chaos parameters and/or further parameters as well is possible.

By way of example, discriminant-analytic methods or neuronal networks are suitable for classifying EEG data by means of multivariate classification functions on the basis of spectral parameters and/or AR parameters and/or Hjorth parameters and/or chaos parameters and/or further parameters as well.

Discriminant-analytic classification methods are suitable for assigning objects to one of a plurality of defined groups on the basis of a sequence of features raised. In the case of the absence EEG stage division, the EEG portions form the objects to be classified, which are characterized by spectral parameters and/or AR parameters and/or Hjorth parameters and/or chaos parameters. For the purposes of calculating suitable classification functions, there are a series of methods, in which a distinction can be made between parametric and non-parametric approaches. Classification functions based on the considered feature values can be derived by means of a sample of objects for which the group belonging is known.

In parametric methods, the assumption is made that the considered feature vector in the various groups follows a multivariate normal distribution. The linear discriminant analysis assumes the equality of the covariance matrices in the individual groups; the quadratic discriminant analysis allows different covariance matrices of the groups to be taken into account. The Mahalanobis distance is used as a distance metric; it constitutes the weighted distance of an observation vector from the group mean values. Then, an object is assigned to the group in which a function of the Mahalanobis distance, which is dependent on the selected method, is the smallest.

If the distribution of the feature vector is unknown, or if it does not have a normal distribution, it is possible to use non-parametric methods for deriving classification rules. A descriptive method is the k-nearest neighbor method. Here, the distances are formed between the feature vector to be classified and all other feature vectors of the available sample, they are ordered according to size and the observation vectors with the k smallest distances are determined, wherein the number k of values taken into account needs to be set in advance. Then, the groups to which these k values belong are determined and the portion thereof of the overall number of measurements in the individual groups is established. The assignment is then carried out to the group in which this portion is the largest.

Compared to parametric methods, this non-parametric method requires an increased computational outlay since the entire original data record needs to be resorted to for classifying an object, while the feature values of an object are inserted into classification functions in the case of parametric methods.

In order to assess the quality of a classification method, use can be made of the associated error rate, wherein the error rate is understood to mean the portion of incorrect classifications. One option for estimating the error rate consists of reclassifying the data. However, the error rate established thus supplies an estimate of the true error rate that is too positive. A more realistic estimate of the error rate is given when the classifications are tested on an independent data record. This can be implemented by splitting the given data record into a training data record for deriving the classification prescription and a test data record for validating the classification. An extreme form of splitting the data consists of the so-called cross validation or the leave-one-out method. In this case, one observation is removed from the data record in each case and the classification is undertaken on the basis of the discriminant function calculated from the remaining data.

If a large number of potential features for deriving discriminant functions are available, it is possible to establish, by way of suitable step-by-step methods, those parameters which ensure a separation of the groups that is as large as possible. To this end, a number of methods are proposed in the literature; by way of example, parameters are included step-by-step in the evaluation, which parameters in each case supply the largest contribution to the group separation on the basis of Wilks's lambda distribution.

The stage division of the anesthesia or intensive care EEG can be carried out in the style of Kugler, who, as mentioned in the introductory part, denotes the awake state with A and the very deep damping of the brain function with F. The intermediate stages B to E can be further subdivided in the process, as shown in table 1 in WO 97/15013 A2. Instead of using the class designations A to F, it is also possible, for example, to use a scale with digits, e.g. 100 to 0.

A further improvement in the stage division is obtained if the age-specific classification functions for a subject are selected from different stored age-dependent classification functions. It was found that the EEG of a human has age-dependent characteristics. Expressed in a simplified manner, e.g. the spectrum shifts to lower frequencies in the awake state with increasing age for adults and e.g. the delta power is reduced during anesthesia. It is possible to reliably make the correct stage division by taking into account age-specific classification functions.

In accordance with an advantageous development of the invention, a specification about the age of the patient, whose EEG curves are recorded, is entered into the evaluation device. The automatic selection of the scheme of the stage division is carried out by the computer taking into account the entered age specification. This is advantageous in that the manual entry of the age of the patient can restrict the range of schemes of stage divisions to be selected probably coming into question. However, it has been shown that uniquely setting the scheme of stage divisions to be selected purely on the basis of the age specification usually does not lead to satisfactory results since humans and their brains develop differently depending on age, and it is therefore not possible to define a specific age boundary at which e.g. the subdivision into stages A to F, as is conventional in adults, can be undertaken in the EEG curves. Examinations show that such a stage division is possible from an age of approximately half a year onward, but the age spread is relatively large. Therefore, it is advantageous in the case of very young children to have a less differentiated stage division underlying this.

In accordance with an advantageous development of the invention, the automatic selection of the scheme of the stage division is carried out by the computer taking into account the recorded EEG curves and/or data derived therefrom. This is advantageous in that a reliable selection of a fitting scheme of the stage division can be carried out automatically, namely on the basis of the curves recorded in any case, such that the use of the evaluation device is further simplified. By way of example, the recorded EEG curves can be taken into account to the extent that the EEG curves are examined in respect of specific characteristic curve patterns or specific statistical data, which can be established from the curves and which are characteristic for specific development phases of EEGs. Thus, the scheme of the stage division can be selected e.g. on the basis of amplitude data, frequency data and/or mean values or time profiles of amplitudes and/or frequencies of the EEG curves.

In accordance with an advantageous development of the invention, a scheme with a smaller number of distinguishable stages of the absence state is selected in the case where a specific minimum portion of low-frequency signal components is identified and a specific minimum portion of high-frequency signal components is not identified in the EEG curves than in the case where a minimum portion of high-frequency signal components is identified, which may be combined with a specific minimum portion of low-frequency signal components. In this case, it is possible, for example in the case of patients who are children and who exhibit a predominantly slow wave pattern with correspondingly low-frequency signal components in the EEG, to select a fitting scheme of the stage division with fewer distinguishable stages. In the case of older patients, who are characterized by more high-frequency signal components in the EEG curves, it is possible to select schemes with adapted, more finely differentiated stage divisions.

Delta waves may occur as low-frequency signal components under the influence of anesthetics/sedatives. If a minimum portion of higher frequency waves is superposed on these low-frequency waves—expressing the effect of anesthetics—, it is possible to make the decision that this is a differentiated EEG. Accordingly, it is then possible to select a scheme with a larger number of distinguishable stages of the absence state. If the EEG only consists of low-frequency waves, then a scheme with a lower number of distinguishable stages should be selected.

If higher frequency activity with a low or nonexistent portion of low-frequency signal components, as is typical, for example, in stages B and C in the case of older children or adults, occurs during the course of a measurement in the case of young children, then a scheme with a relatively large number of distinguishable stages of the absence state is selected.

In accordance with an advantageous development of the invention, a scheme with a relatively large number of distinguishable stages of the absence state can be selected if a certain portion of high-frequency signal components in the EEG curves is identified. However, in the case where "non-identification of a minimum portion of low-frequency signal components" applies and "identification of a specific portion of high-frequency signal components" does not apply, a scheme with a relatively large number of distinguishable stages of the absence state should not be selected, since this could be a virtually completely or completely suppressed EEG ("stage F" with zero lines).

In accordance with one advantageous development of the invention, the computer initially assumes a first scheme with a specific number of distinguishable stages of the absence state and, at an assessment time at which a sufficient amount of EEG data is available, it selects a second scheme of the stage division, which has a smaller or greater number of distinguishable stages of the absence state than the first scheme, if specific characteristics are identified in the EEG curves. Thus, for example, the second scheme of the stage division can be selected if a minimum portion of low-frequency signal components is identified in the EEG curves. If the selection condition, i.e. the identification of specific characteristics, does not occur, the computer can continue, for example, to apply the first scheme or select the first scheme as scheme to be used for automatically carrying out the stage division. Thus, by way of example, the scheme of a stage division for adults can be used as a first scheme, e.g. with the stage division A to F or with the finer division with the stages $A_0, A_1, A_2, B_0, B_1, B_2, C_0, C_1, C_2, D_0, D_1, D_2$, E and F, as described in table 1 of WO 97/15013 A2. By way of example, the second scheme of the stage division can have a division into stages A, E and F. The aforementioned assignment of the stage divisions to the first and the second scheme can also be carried out the other way around.

For the purposes of setting the first scheme, which the computer initially assumes, use can also be made of the entered age specification of the patient. The assumption can be made in the case of very young children, in particular in the case of neonates and premature babies, that a stage division with a reduced number of stages is initially usable. This appears to be the case for all children in the first 2 to 3 months of life, as current EEG analyses by the applicant show. In the case of a corresponding age entry, the evaluation device does not assume the standard division A, B, . . . , F or 100 to 0, but rather a scheme with a reduced stage division. In the case of older children, the evaluation device can initially assume a scheme with a relatively large number of distinguishable stages and then, where necessary, transition to a scheme with a smaller number of distinguishable stages during the measurement.

In accordance with an advantageous development of the invention, at least frequency components in the delta band are judged to be low-frequency signal components of the EEG curves. Additionally, frequency components with frequencies below the delta band can also be judged to be low-frequency signal components. In a development of the invention, frequency components with frequencies above the delta band can be judged to be high-frequency signal components.

The EEG curves in relation to so-called suppression intervals in burst suppression patterns or in the suppression EEG can be evaluated as a further criterion for the automatic selection of a scheme of the stage division. Here, a burst is understood to mean a sequence of signal waves in an EEG curve. Suppression intervals in EEG curves are curve portions in which no bursts occur and the signal has a flat course compared to the signal waves of a burst. The portions between adjacent bursts are referred to as suppression intervals. In accordance with an advantageous development of the invention, an identification of burst suppression patterns can be carried out when evaluating the EEG curves and a scheme of the stage division which, compared to an otherwise selected scheme of the stage division, has a reduced number of distinguishable stages in the absence state can be selected if predetermined characteristics of burst suppression patterns occur in the EEG curves. By way of example, the length of suppression intervals or the burst suppression ratio (BSR) can be used as characteristics of burst suppression patterns. The burst suppression ratio specifies the percentage of an EEG curve portion that consists of suppression intervals. Furthermore, it is possible to use the inter-burst interval (IBI), which is a measure for the distance between bursts, as a characteristic.

In accordance with one advantageous development of the invention, in addition to a standard scheme of the stage division, a further scheme or, depending on the development phase of the patient, a plurality of further schemes of the stage division are selectable by the computer, in particular stage divisions with a smaller number of distinguishable stages of the absence state than the standard scheme. This permits a stage division which is adapted particularly well to the development phase of the EEG.

In particular, recording EEG data up to the assessment point after the commencement of the absence state is advantageous. As a result of this, possible falsifications as a result of EEG data still recorded in the awake state are avoided when selecting an applicable scheme of the stage division. Examinations show that it is practically impossible to evaluate a development-related stage division of an absence EEG on the basis of the awake EEG.

In accordance with an advantageous development of the invention, a specification about the development phase of the EEG is determined on the basis of the selected scheme of the stage division. This specification about the development phase of the EEG can be used further internally in the evaluation device in order, in a manner dependent thereon, to influence certain further evaluations or classification functions of the analysis of the EEG signals. The specification about the development phase of the EEG can also be output, for example to another device by way of an interface of the evaluation device, or it can be depicted visually, e.g. on a display of the evaluation device.

In accordance with an advantageous development of the invention, the EEG curves are analyzed in respect of curve patterns generated by further biosignals and, if at least one such curve pattern is identified, a check is carried out as to whether a different scheme for the stage division than in the case of a non-identification of such curve patterns is to be selected. In this manner, it is possible, for example, to detect signal interference from the outside, artifacts, in particular movement artifacts and potentials typical for epilepsy and it is possible to take these into account, both for the selection of the scheme of the stage division and for the actual stage classification, i.e. the classification function.

In accordance with an advantageous development of the invention, movement artifacts in the recorded EEG curves are established by means of artifact sensors, which may be connected to the evaluation device, and the EEG curves are corrected and/or the stage division is corrected and/or suppressed and/or a different scheme of the stage division is selected on the basis of the established movement artifacts. By way of example, such artifact sensors can be embodied as deformation sensors of EEG electrodes. Such deformation sensors may comprise capacitors, which are changeable by deformation and the capacitance change of which correlates with the deformation of the EEG electrodes.

For the purposes of determining the current stage of the absence state and/or for the purposes of selecting the scheme of the stage division to be used, it is possible either to use the EEG curves directly or to use data derived therefrom. Thus, by way of example, frequency components can be determined by a Fourier analysis or a similar analysis. Amplitude values can be evaluated statistically. It is also possible to determine an amplitude-integrated EEG. The amplitude-integrated EEG is a time-compressed representation of amplitudes of an EEG portion. When calculating the amplitude-integrated EEG, the EEG signal can e.g. be filtered strongly, rectified and smoothed.

In accordance with claim 11, the object set forth at the outset is furthermore achieved by a computer program with program code means, configured to carry out a method of the type described above if the computer program is executed on a computer. In particular, the computer program can be executed on a computer of the evaluation device explained above. In this case, the computer program can be stored on a machine-readable medium, e.g. on a CD or DVD, a memory stick, on an Internet server or on a storage medium of the evaluation device.

In accordance with claim 12, the object set forth at the outset is furthermore achieved by an evaluation device for evaluating an absence EEG, wherein the evaluation device has at least one computer, EEG signal detection means and output means, wherein the evaluation device is configured to carry out a method of the type described above. Thus, by way of example, the evaluation device can be configured to carry out the method by virtue of the computer executing a computer program of the type described above. By way of example, the output means can be an interface of the evaluation device or a means for visual representation, e.g. a display.

Using drawings, the invention is explained in more detail below on the basis of exemplary embodiments.

In detail.

In the figures, the same reference signs are used for elements that correspond to one another.

Figure 1:
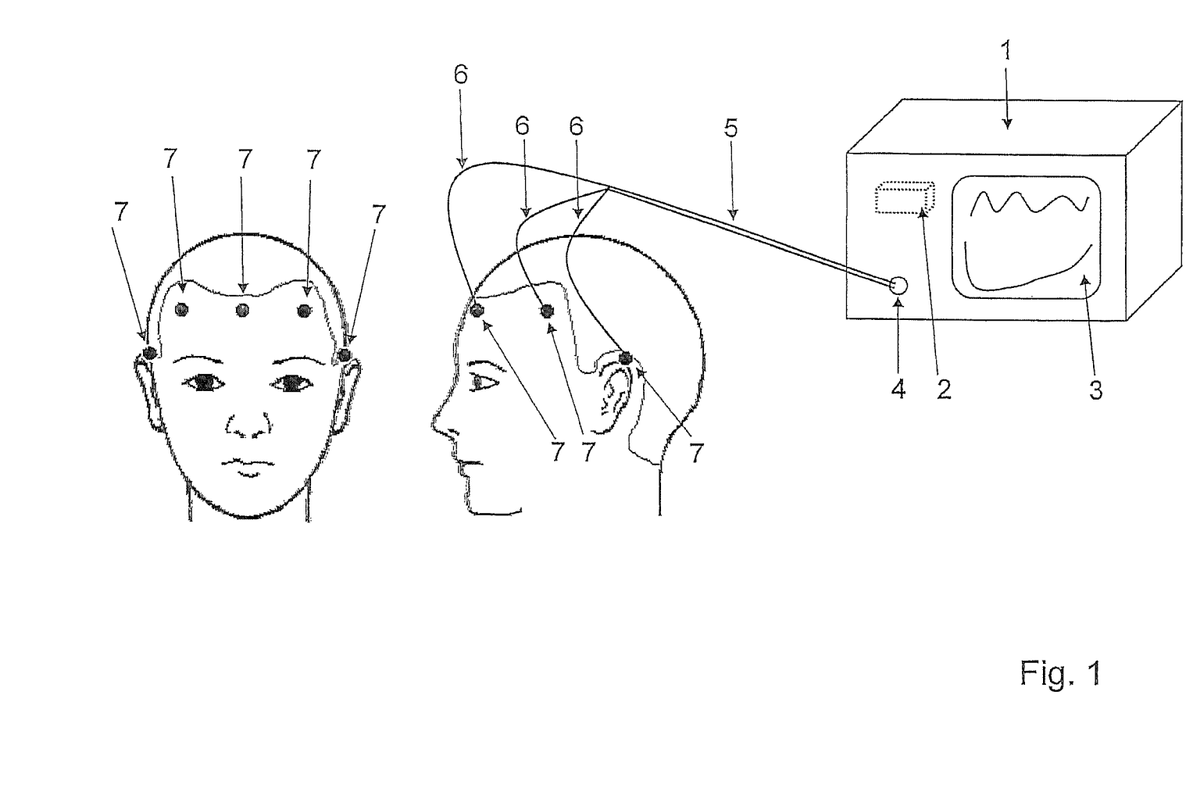
FIG. 1 shows an evaluation device when recording an EEG.

FIG. 1 shows an evaluation device 1 for evaluating an absence EEG. The evaluation device 1 has a computer 2, which may e.g. be embodied as a microprocessor or microcontroller, arranged in the evaluation device, for example on a central printed circuit board. The evaluation device 1 furthermore has a display means 3, for example a display. On the display means 3, curve profiles can be depicted graphically or other data registered and determined therefrom can be reproduced. Furthermore, the evaluation device 1 has an electrical connector 4 which serves to connect EEG electrodes 7, for example by means of plug-in connectors.

FIG. 1 illustrates how a plurality of EEG electrodes 7 are arranged on the head of a patient. The EEG electrodes 7 are connected to the electrical connector 4 of the evaluation device 1 by way of cables 6, which are combined to form a common cable harness 5 in the vicinity of the evaluation device. The common cable harness 5 can be used as one or more artifact sensors for identifying movement artifacts, for example by evaluating the capacitance values present between the cables. To this end, detection means for detecting capacitances between the lines 6 of the cable harness 5 are provided in the evaluation device 1.

Figure 2:
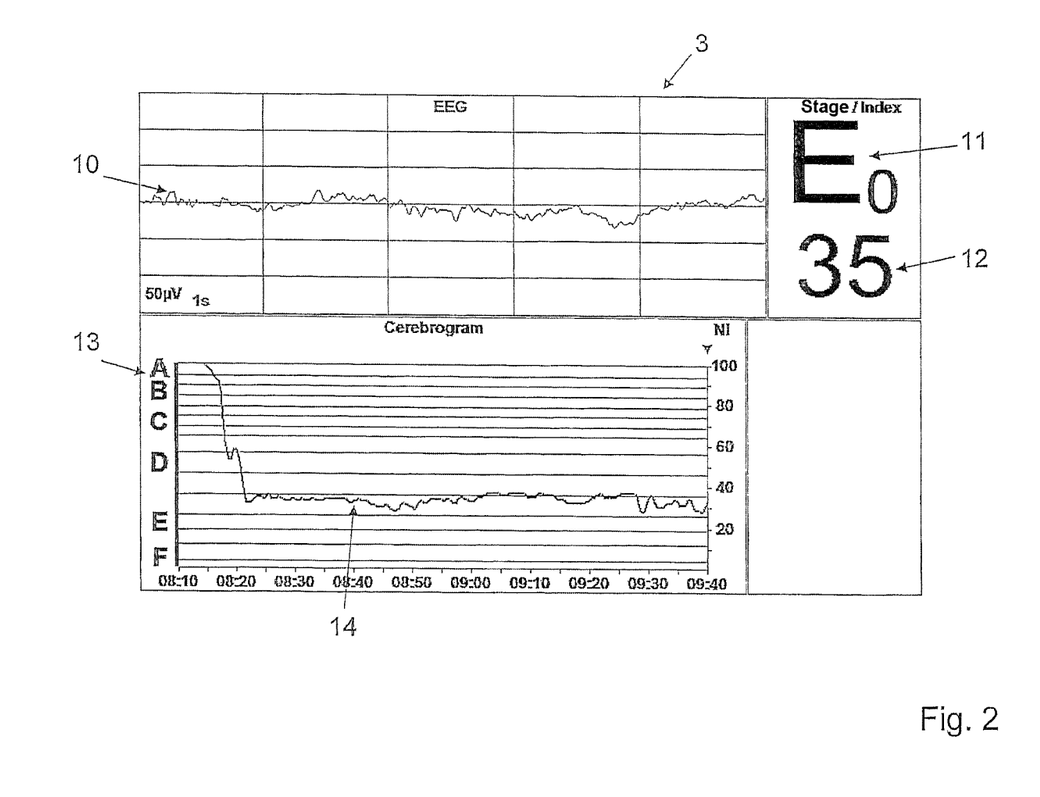
FIG. 2 shows an illustration of EEG curves recorded by the evaluation device and data derived therefrom and FIG. 3 shows an illustration of the procedure when evaluating an absence EEG in the evaluation device.

In an exemplary manner, FIG. 2 shows typical data output on the display means 3 of the evaluation device 1. By way of example, one or more EEG curves 10, as recorded by the EEG sensors 7, can be depicted in an upper window as curve profile over time. The current stage of the absence state, as established by the computer 2 by evaluating the EEG curves, can be displayed in a display region 11. Additionally, the anesthesia or sedation depth can be output as a dimensionless number in the range from 0 to 100 in a display region 12.

The time profile of the established stages, as depicted in region 11, can be specified as a curve profile 14 in a time diagram display bottom right. In the region 13, the distinguishable stages A to F of the selected scheme of the stage division are reproduced on the vertical axis of the diagram. The specification A to F indicates the stage division in the case of an adult patient. In the case of a less-developed EEG, for example in the case of a very young child, a different output, e.g. only the letters A, E and F, can then occur in the region 13 due to a different scheme of the stage division being selected by the computer. It is also possible to use, for example, a scale with digits, e.g. 100 to 0, instead of the class designations A to F.

The following table shows an exemplary assignment between the stages with the class designations A to F and a scale with digits (index values).

| Stage | Index | Dominating EEG characteristics |
|---|---|---|
| A | 100-95 | Alpha waves |
| $B_0$ | 94-90 | Beta waves, theta waves |
| $B_1$ | 89-85 | |
| $B_2$ | 84-80 | |
| $C_0$ | 79-75 | Increasing amount of theta waves |
| $C_1$ | 74-70 | |
| $C_2$ | 69-65 | |
| $D_0$ | 64-57 | Increasing amount of delta waves |
| $D_1$ | 56-47 | |
| $D_2$ | 46-37 | |
| $E_0$ | 36-27 | Continuous, high delta waves |
| $E_1$ | 26-20 | |
| $E_2$ | 19-13 | Transition to the burst suppression pattern |
| $F_0$ | 12-5 | Burst suppression pattern |
| $F_1$ | 4-0 | Continuous EEG suppression |

As already mentioned previously, a stage division with a few stages (in this case e.g. A, E, F) should be used in the case of children with an immature EEG. Either the index values 100-0 could be adapted to the reduced stage division (the entire index range 100-0 would be used) or only part of the index range 100-0 could be used, e.g. use would only be made of the range 100-95 and the range 36-0.

Figure 3:
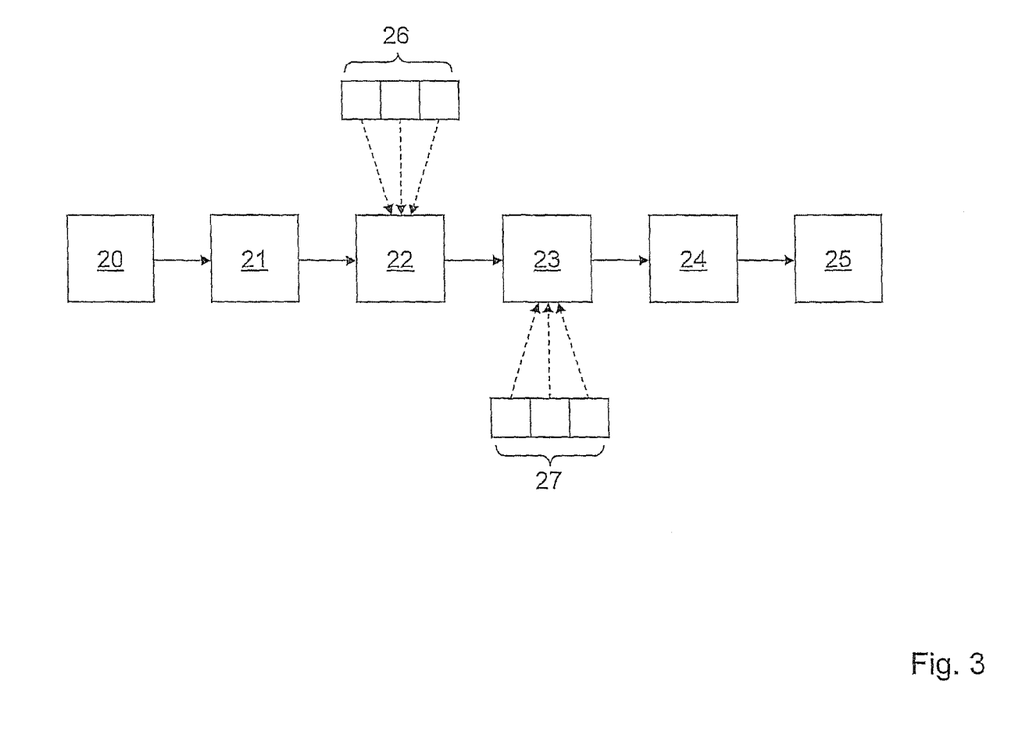

FIG. 3 shows the procedure when automatically evaluating the EEG curves by the computer 2. Blocks 20, 21, 22, 23, 24, 25, reproduced in FIG. 3, in this case specify specific evaluation functions or algorithms, which are executed on the computer 2. Thus, blocks 20, 21, 22, 23, 24, 25 can be embodied, for example, as program sections, program modules or subprograms of a computer program executed by the computer 2.

The EEG curves are read in block 20. In a subsequent block 21, there is a signal analysis of the EEG curves, for example by Fourier transform, determining a power spectrum and/or an amplitude-integrated EEG. In a subsequent block 22, a scheme of the stage division to be applied is selected from a plurality of selectable schemes 26 on the basis of one or more of the criteria still explained below. Three selectable schemes are depicted by the three blocks 26 in an exemplary manner, of which the computer 2 selects one in block 22.

In a subsequent block 23, a classification function is selected for the classification of the EEG curves to be subsequently carried out and for establishing the current stage on the basis of a stage division of the absence EEG. What is illustrated in an exemplary manner is that the computer can select one of three selectable classification functions 27 in block 23. Then, in a subsequent block 24, the EEG curves or data determined therefrom are evaluated on the basis of the selected classification function in such a way that a stage division of the absence EEG is carried out using the scheme of the stage division selected in block 22. The established current stage of the absence state is then output in a subsequent block 25, optionally in addition to further data.

In block 22, the selection of the scheme of the stage division to be used from the available schemes 26 can be carried out on the basis of an age, entered in advance, of the patient whose EEG curves are taken, on the basis of the recorded EEG curves and/or data derived therefrom itself and/or on the basis of previously selected schemes of stage divisions, as is already explained more closely in detail above. In particular, use to this end can be made of EEG curves after the commencement of the absence state. In this manner, there can be a stage division adapted to the development of the EEG or the development of the patient and their age. Analogously thereto, there can be a correspondingly adapted selection of a classification function from the available classification functions 27 in block 23. The criteria during the selection in block 23 can be one or more of the aforementioned criteria.

Accordingly, there is a stage division of the absence EEG in block 24 which is adapted in two ways to the age and development phase of the patient. The stage division in view of the further evaluation of the EEG curves is optimized by the selection of the suitable classification functions in block 23. The data derived therefrom is in this case not always classified with one and the same scheme of the stage division, as in the case of known evaluation devices, but rather it is classified variably on the basis of the scheme of the stage division selected in block 22, which is optimized for the respective age and development phase of the patient. Thus, by way of example, an "adult algorithm" is selected for the classification function in the case of an adult patient. The results established in the process are then classified into one of six stages A to F on the basis of the selected scheme of the stage division. In the case of a very young child, a "child algorithm" would be used as classification function. A less fine scheme with e.g. only three distinguishable stages would be used for the stage division.

The invention claimed is:

1. A method for automatically evaluating an absence electroencephalogram (EEG) from EEG curves which are recorded by an evaluation device, comprising:
   determining by a computer of, associated with, or in communication with the evaluation device a current stage of an absence state of a patient from the EEG curves on the basis of a stage division of the absence EEG,
   wherein a distinction is made in the stage division between stages of a depth of the absence state, and wherein a current stage is output,
   wherein a specific scheme of the stage division is selected by the computer from a plurality of selectable schemes of stage divisions which differ in terms of a number of distinguishable stages of the absence state, and
   wherein the specific scheme of the stage division is used for automatically carrying out the stage division for determining the current stage.

2. The method as claimed in claim 1, wherein the determining steps utilizes a specification about an age of the patient whose EEG curves are recorded entered into the evaluation device, and
   wherein an automatic selection of the specific scheme of the stage division is carried out by the computer taking into account the entered age specification.

3. The method as claimed in claim 1, wherein an automatic selection of the specific scheme of the stage division is carried out by the computer taking into account the recorded EEG curves and/or data derived therefrom.

4. The method as claimed in claim 1, wherein the specific scheme selected by the computer includes a smaller number of distinguishable stages of the absence state for the determining step in the case of patients who are children and who exhibit a predominantly slow wave pattern with correspondingly low-frequency signal components.

5. The method as claimed in claim 1 wherein the computer initially assumes a first scheme with a specific number of distinguishable stages of the absence state and, wherein at an assessment time at which EEG data are available, the computer selects a second scheme of the stage division as the specific scheme, wherein the specific scheme has a smaller or greater number of distinguishable stages of the absence state than the first scheme.

6. The method as claimed in claim 5 wherein the specific scheme of stage division depends on whether the patient is an adult or a child.

7. The method of claim 6 wherein the specific scheme of stage division has a smaller number of stages in the case of a child or has a higher number of stages in the case of an adult.

8. The method as claimed in claim 1 wherein at least frequency components in a delta band are judged to be low-frequency signal components of the EEG curves.

9. The method as claimed in claim 1 further comprising selecting the specific scheme of the stage division based on the age of the patient.

10. The method as claimed in claim 1 further comprising identifying curve patterns in the EEG curves indicative of movement artifacts.

11. The method of claim 10 further comprising determining whether a different scheme for the stage division is to be selected based on curve patterns identified as being indicative of movement.

12. The method as claimed in claim 1 further comprising correcting for movement artifacts in the recorded EEG curves established by artifact sensors by correcting the EEG curves and/or correcting the stage division and/or selecting a different scheme of the stage division based on the established movement artifacts.

13. A computer program stored on a non-transient machine-readable medium, configured to carry out a method as recited in claim 1 using a computer of, associated with or in communication with an evaluation device for automatically evaluating an absence EEG.

14. An evaluation device for evaluating an absence EEG, comprising:

at least one computer;

an EEG signal detection means; and output means, wherein the evaluation device is configured to perform the method of claim 1.

* * * * *